(12) United States Patent
Kawanami

(10) Patent No.: US 9,175,012 B2
(45) Date of Patent: Nov. 3, 2015

(54) METHOD FOR PRODUCING OPTICALLY ACTIVE DIAMINE DERIVATIVE

(75) Inventor: Koutarou Kawanami, Hiratsuka (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/231,081

(22) Filed: Sep. 13, 2011

(65) Prior Publication Data

US 2012/0035369 A1 Feb. 9, 2012

Related U.S. Application Data

(63) Continuation of application No. PCT/JP2010/053976, filed on Mar. 10, 2010.

(30) Foreign Application Priority Data

Mar. 13, 2009 (JP) ................................ 2009-061708

(51) Int. Cl.

| C07C 247/14 | (2006.01) |
|---|---|
| C07D 513/04 | (2006.01) |
| C07B 53/00 | (2006.01) |
| C07B 55/00 | (2006.01) |
| C07C 269/06 | (2006.01) |
| C07C 269/08 | (2006.01) |

(52) U.S. Cl.
CPC .............. *C07D 513/04* (2013.01); *C07B 53/00* (2013.01); *C07B 55/00* (2013.01); *C07C 247/14* (2013.01); *C07C 269/06* (2013.01); *C07C 269/08* (2013.01)

(58) Field of Classification Search
CPC ............................. C07C 247/14; C07D 513/04
See application file for complete search history.

(56) References Cited

U.S. PATENT DOCUMENTS

| 4,582,570 A | 4/1986 | Mix |
| 5,055,600 A | 10/1991 | Wagner |
| 5,149,855 A | 9/1992 | Sakimae et al. |
| 5,677,469 A | 10/1997 | van Eikeren et al. |
| 6,353,096 B1 | 3/2002 | Leon |

(Continued)

FOREIGN PATENT DOCUMENTS

| JP | 4-227629 | 8/1992 |
| JP | 11-180899 | 7/1999 |

(Continued)

OTHER PUBLICATIONS

Chiappe et. al. "Nucleophilic Displacement Reactions in Ionic Liquids: Substrate and Solvent Effect in the Reaction of NaN3 and KCN with Alkyl Halides and Tosylates" Journal of Organic Chemistry 2003, 68, 6710-6715.*

Betti, C. et. al. "Reactivity of anionic nucleophiles in ionic liquids and molecular solvents" Tetrahedron 2008, 64, 1689.*

(Continued)

*Primary Examiner* — David K O Dell
(74) *Attorney, Agent, or Firm* — Locke Lord LLP

(57) ABSTRACT

The problem to be solved is to provide an important intermediate for production of an FXa inhibitor. The solution thereto is a method for industrially producing a compound (1) or a compound (4), comprising: [Step 1]: adding a quaternary ammonium salt and a metal azide salt to water to prepare an aqueous solution of an azidification reagent complex comprising quaternary ammonium salt-metal azide salt, and subsequently dehydrating the aqueous solution using an aromatic hydrocarbon solvent to form a mixed solution of the azidification reagent complex comprising quaternary ammonium salt-metal azide salt and the aromatic hydrocarbon solvent with a water content of 0.2% or less; and [Step 2]: adding, to the mixed solution prepared in [Step 1], a compound (2) wherein L represents a leaving group.

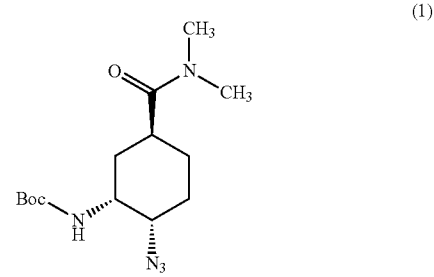

(1)

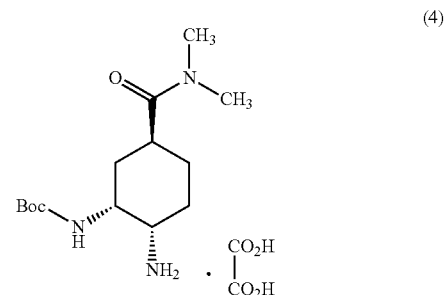

(4)

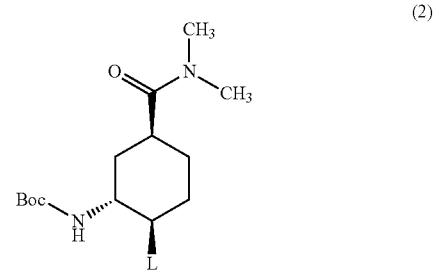

(2)

18 Claims, No Drawings

(56) References Cited

U.S. PATENT DOCUMENTS

| | | |
|---|---|---|
| 7,192,968 B2 | 3/2007 | Yoshino et al. |
| 7,342,014 B2 | 3/2008 | Ohta et al. |
| 7,365,205 B2 | 4/2008 | Ohta et al. |
| 7,576,135 B2 | 8/2009 | Ohta et al. |
| 7,674,904 B2 | 3/2010 | Doshan et al. |
| 8,357,808 B2 | 1/2013 | Koyama |
| 8,394,821 B2 | 3/2013 | Ono |
| 8,404,847 B2 | 3/2013 | Koyama |
| 8,449,896 B2 | 5/2013 | Kamada |
| 8,541,443 B2 | 9/2013 | Suzuki |
| 8,901,345 B2 | 12/2014 | Kawanami |
| 2004/0122063 A1 | 6/2004 | Yoshino et al. |
| 2005/0020645 A1 | 1/2005 | Ohta et al. |
| 2005/0119486 A1 | 6/2005 | Ohta et al. |
| 2005/0245565 A1 | 11/2005 | Ohta et al. |
| 2006/0252837 A1 | 11/2006 | Ohta et al. |
| 2006/0275357 A1 | 12/2006 | Oomura et al. |
| 2007/0135476 A1 | 6/2007 | Nagasawa et al. |
| 2008/0015215 A1 | 1/2008 | Ohta et al. |
| 2009/0105491 A1 | 4/2009 | Sato et al. |
| 2009/0192313 A1 | 7/2009 | Nagasawa et al. |
| 2009/0270446 A1 | 10/2009 | Ohta et al. |
| 2009/0281074 A1 | 11/2009 | Ohta et al. |
| 2010/0081685 A1 | 4/2010 | Kojima et al. |
| 2011/0257401 A1 | 10/2011 | Sato |
| 2011/0275666 A1 | 11/2011 | Abiko |
| 2012/0053349 A1 | 3/2012 | Yoshino |
| 2013/0158069 A1 | 6/2013 | Kimura |
| 2013/0184308 A1 | 7/2013 | Abiko |
| 2014/0100244 A1 | 4/2014 | Kimura |
| 2014/0371262 A1 | 12/2014 | Kimura |

FOREIGN PATENT DOCUMENTS

| | | |
|---|---|---|
| JP | 2000-344735 | 12/2000 |
| JP | 2001-151724 | 6/2001 |
| JP | 2008-542287 | 11/2008 |
| WO | WO 01/74774 | 10/2001 |
| WO | WO 03/000657 | 1/2003 |
| WO | WO 03/000680 | 1/2003 |
| WO | WO 03/016302 | 2/2003 |
| WO | WO 2004/058715 | 7/2004 |
| WO | WO 2005/047296 | 5/2005 |
| WO | WO 2007/032498 | 3/2007 |
| WO | WO 2008/129846 | 10/2008 |
| WO | WO 2008/156159 | 12/2008 |

OTHER PUBLICATIONS

Morrison, K. "Physical Science Level 3" Pearson Education: Capetown, 2008, pp. 16-18.*

Dubois, D., et al., "Clinical calorimetry. X. A formula to estimate the approximate surface area if the height and weight be known" *Archives of Internal Medicine*, 17, 863-71 (1916).

Elodi, S., et al., "Optimization of conditions for the catalytic effect of the factor IXa-factor VIII complex: probable role of the complex in the amplification of blood coagulation" *Thrombosis Research*, 15(5-6), 617-29 (1979).

Fujimoto, et al., "Studies on the physical surface area of Japanese: Part 18 calculation formulas in three stages over all age" *Japanese Journal of Hygene*, vol. 23(5): 443-450 (1968)—(Contains an English Abstract).

Furugohri, T., et al., "DU-176b, A potent and orally active factor Xa inhibitor: In vitro and in vivo pharmacological profiles" *Journal of Thrombosis and Haemostasis*, 6(9), 1542-1549 (2008).

Goldberg, SI, et al., "Correlation of configuration and rotatory direction for several 4-substituted cyclohexenes" *Journal of Organic Chemistry*, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" *Blood* 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" *Journal of Clinical Pharmacology*, 49(9), 1125 (2009).

Mendell, J., et al., "Thorough QT/QTC study with edoxaban to evaluate effect of therapeutic and supratherapeutic exposure on QTC interval duration in healthy subjects" *Journal of Clinical pharmacology* 49(9), 1122 (2009).

Mould, D., et al., "A population pharmacokinetic pharmacodynamic and logistic regression analysis of lotrafiban in patients" *Clinical Pharmacology and Therapeutics* 69(4), 210-222 (2001).

Mueck, W., et al., "Population pharmacokinetics and pharmacodynamic of rivaroxaban—an oral, direct factor Xa inhibitor—in patients undergoing major orthopaedic surgery" *Clinical Pharmacokinetics*, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane® and Clexane® Forte, Clexane ® PI MKT, #6178v16, pp. 1-19 (2008).

Ridout, G., et al., "Effect of renal function on edoxaban pharmacokinetics (PK) and on population PK/PK-PD model" *Journal of Clinical Pharmcology* 49(9), 1124 (2009).

Schwartz, Hm, et al., "Predicting the Enantiomeric Selectivity of Chymotrypsin. Homologous Series of Ester Substrates" *J. Am. Chem. Soc.*, 100, 5199-5203, (1978).

Sixma JJ, et al., "The ideal anti-thrombotic drug" *Thrombosis research*, 68(6), 507-12 (1992).

Takahashi, H. "3.Warfarin Oto no kojinsa" *Kessen to Junkan*, 14(3), 198-202 (2006) (English Translation Provided).

Tanyeli, C, et al., "Enzyme catalyzed reverse enantiomeric separation of methyl (±)-3-cyclohexene-1-carboxylate" *Tetrahedron: Asymmetry*, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" *Thrombosis and Haemostasis*, 90(6), 1163-1172 (2003).

International Preliminary Report on Patentability, issued in PCT/JP2009/070613, mailed Jul. 5, 2011.

International Search Report, issued in PCT/JP2009/070613, mailed Feb. 16, 2010.

Written Opinion of the International Searching Authority, issued in PCT/JP2009/070613, mailed Jul. 5, 2011.

International Preliminary Report on Patentability, issued in PCT/JP2009/070874, mailed Jul. 5, 2011.

International Search Report, issued in PCT/JP2009/070874, mailed Mar. 23, 2010.

Written Opinion of the International Searching Authority, issued in PCT/JP2009/070874, mailed Jul. 5, 2011.

International Preliminary Report on Patentability, issued in PCT/JP2009/071016, mailed Jul. 5, 2011.

International Search Report, issued in PCT/JP2009/071016, mailed Feb. 16, 2010.

Written Opinion of the International Searching Authority, issued in PCT/JP2009/071016, mailed Jul. 5, 2011.

International Preliminary Report on Patentability, issued in PCT/JP2010/050128, mailed Aug. 16, 2011.

International Search Report, issued in PCT/JP2010/050128, mailed Apr. 6, 2010.

Written Opinion of the International Searching Authority, issued in PCT/JP2010/050128, mailed Aug. 16, 2011.

International Preliminary Report on Patentability, issued in PCT/JP2010/057990, mailed Dec. 12, 2011.

International Search Report, issued in PCT/JP2010/057990, mailed Jun. 8, 2010.

Written Opinion of the International Searching Authority, issued in PCT/JP2010/057990, mailed Dec. 12, 2011.

International Preliminary Report on Patentability, issued in PCT/JP2010/060261, mailed Dec. 20, 2011.

International Search Report, issued in PCT/JP2010/060261, mailed Sep. 21, 2010.

(56) References Cited

OTHER PUBLICATIONS

Written Opinion of the International Searching Authority, issued in PCT/JP2010/060261, mailed Dec. 20, 2011.
Patani, et al., "Bioisosterism: A rational approach in drug design", Chem. Rev. 1996, 3147-3176.
Blagden, N., et al. "Crystal engineering of active pharmaceutical ingredients to improve solubility and dissolution rates." *Advanced Drug Delivery Reviews*, 59:603-616 (2007).
Serajuddin, a., "Salt formation to improve drug solubility." *Advanced Drug Delivery Reviews*, 59:617-630 (2007).
Ohta, T., et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).
PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Supplementary European Search Report mailed Jun. 4, 2012 in EP Application No. 09 83 3467, which corresponds to related U.S. Appl. No. 13/163,287.
Furugohri, T, et al, "Pharmaceutical Characterization, Antithromboti and Bleeding Effects of DU-176b", Journal of Thrombosis and Haemostasis, 3(supp. 1), Abstract P1110, (2005).
Zafar, UM, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).
Walker, MB, "Understanding the PT-INR Test", obtained from the internet www.vclotacare.com/ptinr.aspx (retrieved Apr. 24, 2012).
Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).
Thomas, M., et al, "Management of Venous Thromboembolism", *Arch Intern Med.*, 163:759-768 (2003).
Turpie, AGG., "Oral, direct factor Xa inhibitors in development for the prevention and treatment of thromboembolic diseases", *Arteriosclerosis, Thrombosis, and Vascular Biology*, 27:1238-1247 (2007).
De Caterina, R, et al. "Anticoagulants in heart disease: current status and perspectives", European Heart Journal 28:880-913 (2007).

Dyke, CK., "First experience with direct factor Xa inhibition in patients with stable coronary disease: a pharmacokinetic and pharmacodynamics evaluation", *Circulation.*, 105:2385-2391 (2002).
Iba, T., et al., "Factor Xa-inhibitor (DX-9065a) modulates the leukocyte-endothelial cell interaction in endotoxemic rat", *Shock.*, 17(2):159-162 (2002).
Office of Generic Drugs, "Scoring Configuration of Generic Drug Products", dated Nov. 1, 1995; www.fda.gov/downloads/AboutFDA/CentersOffices/CDER/ManualofPoliciesProcedures/ucm079779.pdf; accessed Sep. 6, 2012; cited in related U.S. Appl. No. 13/163,287.
Kozma, D., "CRC Handbook of Optical Resolutions Via Diastereomeric Salt Formation", CRC Press: Washington, DC, Chapters 4, 5, and 6 (2002).
Murakami, "Asymmetric Transformation of a Racemic a-(Phthalimidooxy)arylacetic Ester by a Combination of Preferential Crystallization and Simultaneous Racemization" *Chirality* 5141-48 (1993).
International Search Report, issued in related International Application No. PCT/JP2011/055955, mailed May 24, 2011.
Written Opinion of the International Searching Authority, issued in related International Application No. PCT/JP2011/055955, mailed May 24, 2011.
Communication pursuant to Rule 114(2) EPC (Third-Party Observation) as issued in the corresponding European Application No. 10750859.0, dated Dec. 10, 2014.
Supplementary European Search Report and Opinion, as issued in corresponding European Application No. 10750859.0, dated Jul. 3, 2012.
Takeishi, M, et al. "Kinetic effects of surfactants on a polymer reaction in a nonaqueous system: Nucleophilic substitution of poly(vinyl chloride) with the azide ion." Makromol. Chem., 167: 261-272. (1973).
Dean, J. "Lange's Handbook of Chemistry"; McGraw-Hill, Inc. (1999), 15th Ed., p. 5.62, Table 5.11.
Weitz, et al., "Randomized, Parallel Group, Multicenter, Multinational Study Evaluating Safety of DU-176b Compared with Warfarin in Subjects with Non-Valvular Atrial Fibrillation" Blood (ASH Annual Meeting Abstracts) 112: Abstract 33 (Dec. 9, 2008).
Halabi, et al., "Effects of renal impairment on the pharmacology of rivaroxaban (BAY 59-7939)—An oral, direct, Factor Xa inhibitor"; Blood (ASH Annual Meeting Abstracts) 108: Abstract 913 (Dec. 9, 2008).
Anonymous, 50th ASH Annual Meeting Program, (Dec. 9, 2008) https://ash.confex.com/ash/2008/webprogram/start.html, accessed Mar. 18, 2015.
Anonymous, Clinical Trial NCT00504556, A phase 2, randomized, parallel group, multi center, multi national study for the evaluation of safety of four fixed dose regimens of DU-176b in subjects with non-valvular atrial fibrillation; (updated Mar. 31, 2008).
Allan, R., "Synthesis of analogs of GABA. VI. Stereoisomers of cis-3-aminocyclohexanecarboxylic acid" Australian Journal of Chemistry, 34(10):2231-36 (1981) (Abstract only).

\* cited by examiner

METHOD FOR PRODUCING OPTICALLY ACTIVE DIAMINE DERIVATIVE

This application is a continuation of International Application No. PCT/JP2010/053976, filed on Mar. 10, 2010, entitled "METHOD FOR PRODUCING OPTICALLY ACTIVE DIAMINE DERIVATIVE", which claims the benefit of Japanese Patent Application Number JP 2009-061708, filed on Mar. 13, 2009, all of which are hereby incorporated by reference.

FIELD OF THE INVENTION

The present invention relates to a method for industrially producing an optically active diamine derivative that is important for production of a compound (A) shown below as an activated blood coagulation factor X (FXa) inhibitor or a pharmacologically acceptable salt thereof, or a hydrate thereof.

BACKGROUND OF THE INVENTION

Compound (A) or a pharmacologically acceptable salt thereof, or a hydrate thereof is a compound that exhibits an FXa inhibitory effect, as disclosed in Patent Literatures 1 to 3, and is useful as preventive and/or therapeutic drugs for thrombotic and/or embolic diseases.

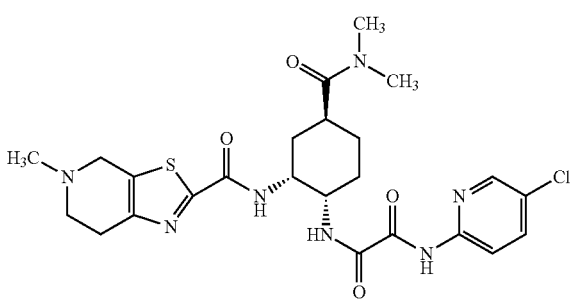

(A)

The pamphlet of International Publication No. WO 2007/032498 discloses a method for producing compound (A) using an azide derivative compound (1) and an optically active diamine derivative compound (3) as production intermediates. This pamphlet discloses a method comprising treating a compound (2a) with sodium azide and 1-dodecylpyridinium chloride in an amide solvent such as N,N-dimethylacetamide (DMAC) to produce compound (1).

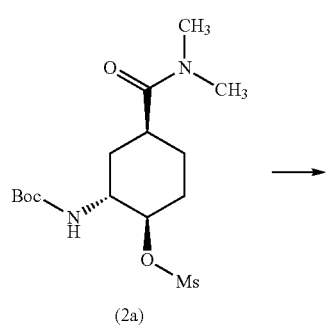

(2a)

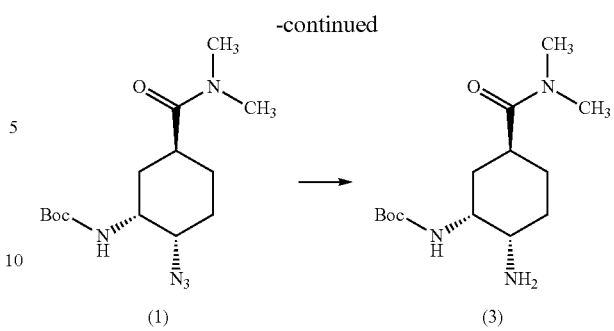

(1) → (3)

wherein Boc represents a tert-butoxycarbonyl group; and Ms represents a methanesulfonyl group.

CITATION LIST

Patent Literatures

Patent Literature 1: International Publication No. WO 2004/058715
Patent Literature 2: International Publication No. WO 2003/016302
Patent Literature 3: International Publication No. WO 2003/000680
Patent Literature 4: International Publication No. WO 2007/032498

SUMMARY OF INVENTION

Technical Problem

The method for producing compound (1), an optically active azide derivative, disclosed in the pamphlet of International Publication No. WO 2007/032498 results in yields as low as 30% or less. This method although using a reduced amount of a dangerous reagent, the metal azide salt, may be available on an industrial scale as long as its yield can be improved. Moreover, the highly polar amide solvent used as a reaction solvent in the conventional method is probably responsible for reduction in yield caused by loss of the product compound (1) during extraction.

Thus, an object of the present invention is to solve these problems and to provide a novel method for industrially producing compound (1) that is an important synthetic intermediate for production of compound (A).

The present inventors have conducted diligent studies over the years with the aim of improving the yield of compound (1).

As a result, the present inventors have completed the present invention by finding that the yield of compound (1) is drastically improved by dissolving a quaternary ammonium salt and a metal azide salt in water to prepare an aqueous solution of an azidification reagent complex comprising quaternary ammonium salt-metal azide salt, subsequently subjecting the aqueous solution of the azidification reagent complex to azeotropic dehydration using an aromatic hydrocarbon solvent to prepare a mixed solution of the azidification reagent complex and the aromatic hydrocarbon solvent with a water content of 0.2% or less, and treating this mixed solution with a compound (2).

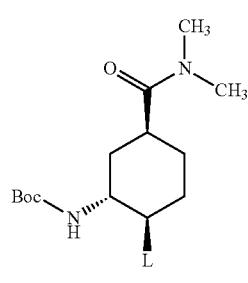

(2)

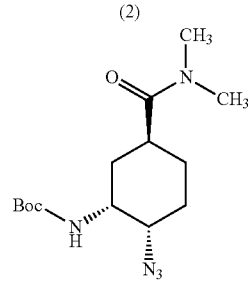

(1)

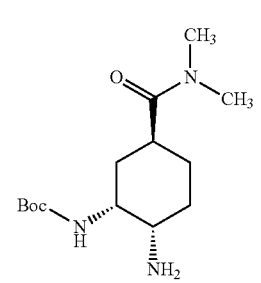

(3)

wherein Boc is as defined above; and L represents a leaving group, wherein the leaving group represents a (C1 to C2 alkyl)sulfonyloxy group (wherein the C1 to C2 alkyl group may have one or more identical or different halogeno groups as substituents) or a benzenesulfonyloxy group (wherein the benzene ring may have one or more identical or different groups as substituents selected from a halogeno group, a methyl group, and a nitro group).

Solution to Problem

The present invention provides (1) to (21) shown below.

(1) A method for producing a compound (1) represented by the following formula:

(1)

wherein Boc represents a tert-butoxycarbonyl group, the method comprising:

[Step 1]: adding a quaternary ammonium salt and a metal azide salt to water to prepare an aqueous solution of an azidification reagent complex comprising quaternary ammonium salt-metal azide salt, and subsequently dehydrating the aqueous solution using an aromatic hydrocarbon solvent to form a mixed solution of the azidification reagent complex comprising quaternary ammonium salt-metal azide salt and the aromatic hydrocarbon solvent with a water content of 0.2% or less; and

[Step 2]: adding, to the mixed solution prepared in [Step 1], a compound (2) represented by the following formula:

(2)

wherein Boc is as defined above; and L represents a leaving group, wherein the leaving group represents a (C1 to C2 alkyl)sulfonyloxy group (wherein the C1 to C2 alkyl group may have one or more identical or different halogeno groups as substituents) or a benzenesulfonyloxy group (wherein the benzene ring may have one or more identical or different groups as substituents selected from a halogeno group, a methyl group, and a nitro group).

(2) The production method according to (1), wherein L is a methanesulfonyloxy group or an ethanesulfonyloxy group.

(3) The production method according to (1), wherein L is a methanesulfonyloxy group.

(4) The production method according to any one of (1) to (3), wherein the quaternary ammonium salt is a pyridinium salt.

(5) The production method according to any one of (1) to (3), wherein the quaternary ammonium salt is a 1-(C1 to C20 alkyl)pyridinium salt.

(6) The production method according to any one of (1) to (3), wherein the quaternary ammonium salt is a 1-dodecylpyridinium salt.

(7) The production method according to any one of (1) to (3), wherein the quaternary ammonium salt is 1-dodecylpyridinium chloride.

(8) The production method according to any one of (1) to (7), wherein the amount of the quaternary ammonium salt used is stoichiometrically in the range of 0.45 to 0.55 molar equivalent with respect to compound (2).

(9) The production method according to any one of (1) to (8), wherein the metal azide salt is sodium azide or lithium azide.

(10) The production method according to any one of (1) to (9), wherein the amount of the metal azide salt used is stoichiometrically in the range of 1.8 to 2.2 molar equivalents with respect to compound (2).

(11) The production method according to any one of (1) to (10), wherein the aromatic hydrocarbon solvent is one selected from benzene, toluene, xylene, chlorobenzene, and dichlorobenzene or a mixed solvent of two or more thereof.

(12) The production method according to any one of (1) to (10), wherein the aromatic hydrocarbon solvent is toluene.

(13) The production method according to (1), wherein the preparation of the aqueous solution of the azidification reagent complex is performed by adding a quaternary ammonium salt and a metal azide salt to water and then stirring the mixture at an internal temperature of 20 to 40° C.

(14) The production method according to (13), wherein the stirring is performed for 0.5 hour or longer.

(15) The production method according to (1), wherein the dehydration is azeotropic dehydration using the aromatic hydrocarbon solvent.
(16) The production method according to (15), wherein the azeotropic dehydration is performed by adding dropwise the aqueous solution of the azidification reagent complex to the aromatic hydrocarbon solvent under heating.
(17) The production method according to (1), wherein [Step 1] comprises
adding the quaternary ammonium salt and the metal azide salt to water and stirring the mixture at an internal temperature of 20 to 40° C. for 0.5 hour or longer to prepare the aqueous solution of the azidification reagent complex comprising quaternary ammonium salt-metal azide salt, and
subsequently performing azeotropic dehydration by adding dropwise the aqueous solution to the aromatic hydrocarbon solvent under heating
to prepare a mixed solution of the azidification reagent complex and the aromatic hydrocarbon solvent with a water content of 0.2% or less.
(18) A method for producing a compound (4) represented by the following formula:

(4)

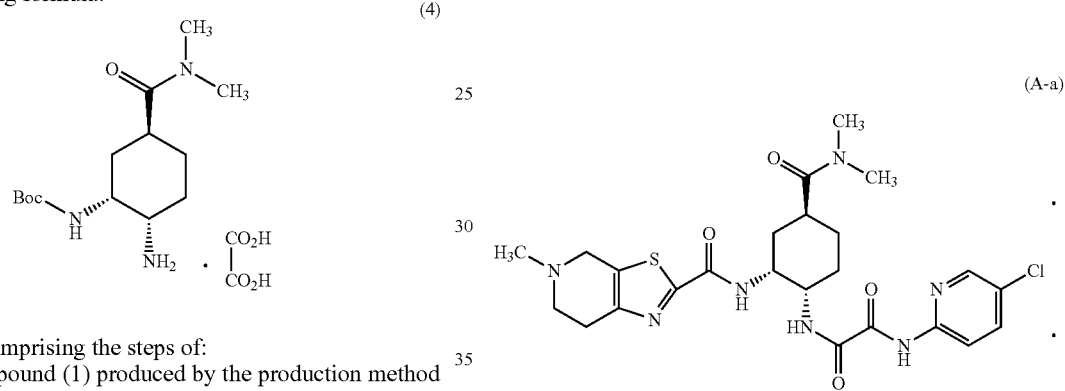

the method comprising the steps of:
reducing compound (1) produced by the production method according to (1):

(1)

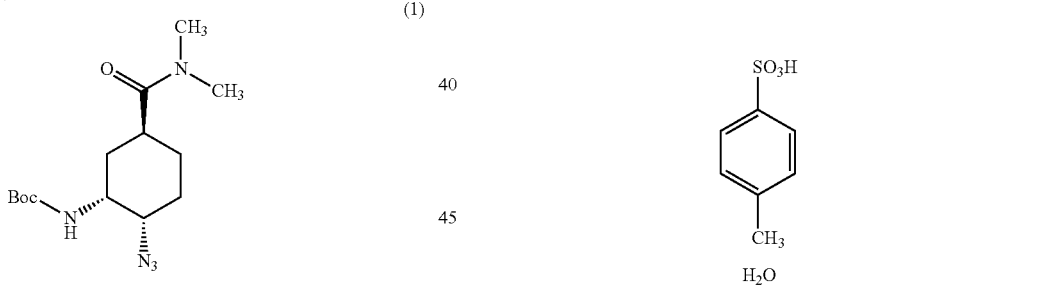

wherein Boc is as defined above,
to obtain a compound (3) represented by the following formula or a salt thereof, or a solvate thereof:

(3)

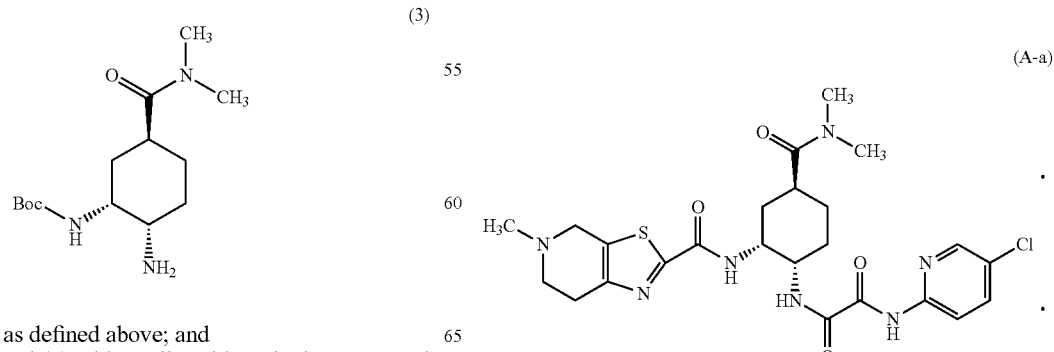

wherein Boc is as defined above; and
treating compound (3) with oxalic acid to obtain compound (4).

(19) The method for producing a compound (1) represented by the following formula according to (1):

(1)

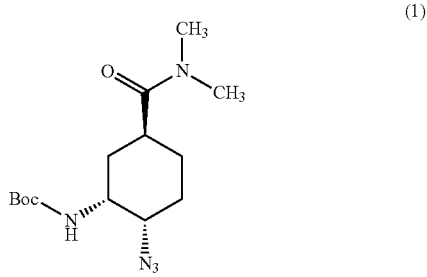 [SMILES: CN(C)C(=O)[C@H]1CC[C@H](N=[N+]=[N-])[C@H](NC(=O)OC(C)(C)C)C1]

wherein Boc is as defined above,
wherein compound (1) is used as a synthetic intermediate for production of a compound (A-a) represented by the following formula:

(A-a)

(20) A method for producing a compound (A-a) represented by the following formula:

(A-a)

-continued

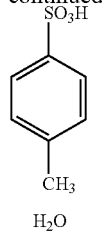

comprising using compound (1) produced by the production method according to (1).

(21) A method for producing a compound (A-a) represented by the following formula:

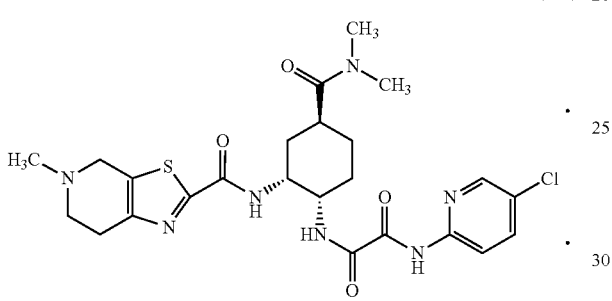

(A-a)

comprising using compound (1) produced by the production method according to (1):

the method comprising the steps of:

reducing compound (1) represented by the following formula:

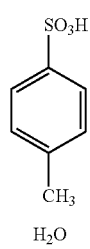

(1)

wherein Boc is as defined above, to obtain a compound (3) represented by the following formula or a salt thereof, or a solvate thereof:

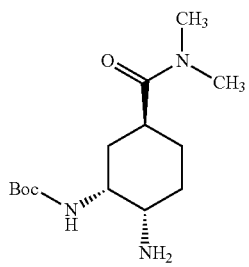

(3)

wherein Boc is as defined above;

treating compound (3) or the salt thereof, or the solvate thereof with oxalic acid to obtain a compound (4) represented by the following formula:

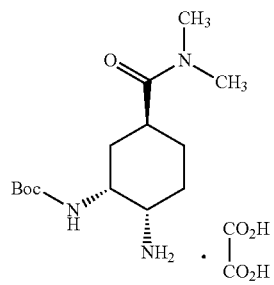

(4)

wherein Boc is as defined above;

treating compound (4) with a compound (7) represented by the following formula:

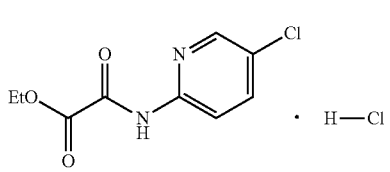

(7)

in the presence of a base to obtain a compound (8) represented by the following formula:

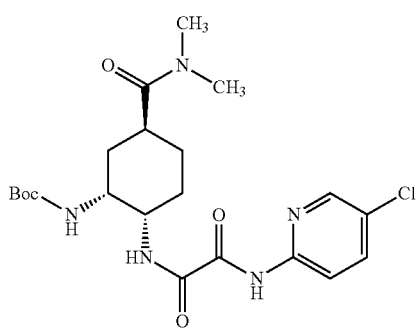

(8)

wherein Boc is as defined above;

deprotecting a Boc group in compound (8) to obtain a compound (9) represented by the following formula or a salt thereof:

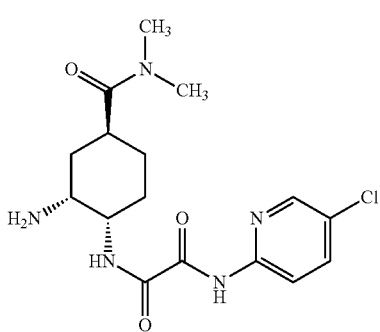

(9)

condensing compound (9) or the salt thereof with a compound (10) represented by the following formula:

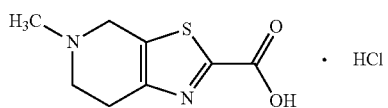

(10)

to obtain a compound (A) represented by the following formula:

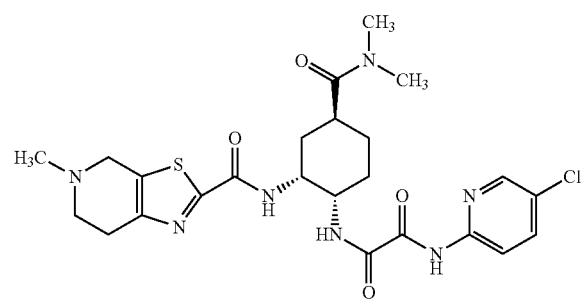

(A)

and
treating compound (A) with p-toluenesulfonic acid or a hydrate thereof to obtain compound (A-a).

Advantageous Effects of Invention

The present invention is useful because optically active azide derivative compound (1) that is an intermediate for production of compound (A) known as an FXa inhibitor can be obtained at a yield of 71 to 75%. Specifically, the production method of the present invention is useful because the yield can be improved drastically compared with the conventional method. Thus, the production method of the present invention is useful as a method for producing compound (A) useful as an FXa inhibitor.

DETAILED DESCRIPTION

Hereinafter, the present invention will be described in detail.
A halogeno group according to the present invention means a fluoro, chloro, or bromo group.
A C1 to C20 alkyl group according to the present invention means a linear or branched alkyl group having 1 to 20 carbon atoms. Examples thereof can include methyl, ethyl, n-propyl, isopropyl, n-butyl, pentyl, hexyl, heptyl, octyl, nonyl, decyl, dodecyl, tridecyl, tetradecyl, pentadecyl, hexadecyl, heptadecyl, octadecyl, nonadecyl, and icosyl groups.

A specific FXa inhibitor according to the present specification is preferably, for example, compound (A) described above. Compound (A) may be a free form (free base) or a hydrate thereof or may be a pharmacologically acceptable salt or a hydrate of the salt.

Examples of the salt of compound (A) include hydrochloride, sulfate, hydrobromide, hydroiodide, phosphate, nitrate, benzoate, methanesulfonate, 2-hydroxyethanesulfonate, p-toluenesulfonate, acetate, propanoate, oxalate, malonate, succinate, glutarate, adipate, tartrate, maleate, fumarate, malate, and mandelate.

The salt of compound (A) is preferably hydrochloride or p-toluenesulfonate,
particularly preferably p-toluenesulfonate.

Compound (A) or a salt thereof, or a hydrate thereof is preferably
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide hydrochloride;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate; or
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate,
particularly preferably
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate (A-a).

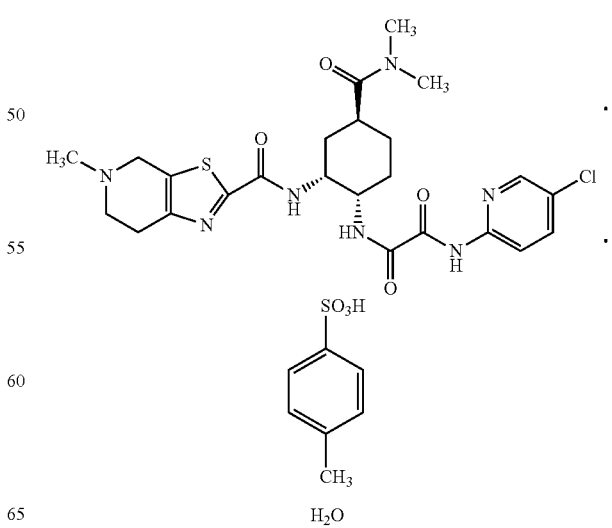

(A-a)

Hereinafter, the production method of the present invention will be described in detail.

The optically active azide derivative compound (1) of the present invention can be produced from compound (2) by the following [Step 1] and [Step 2]:

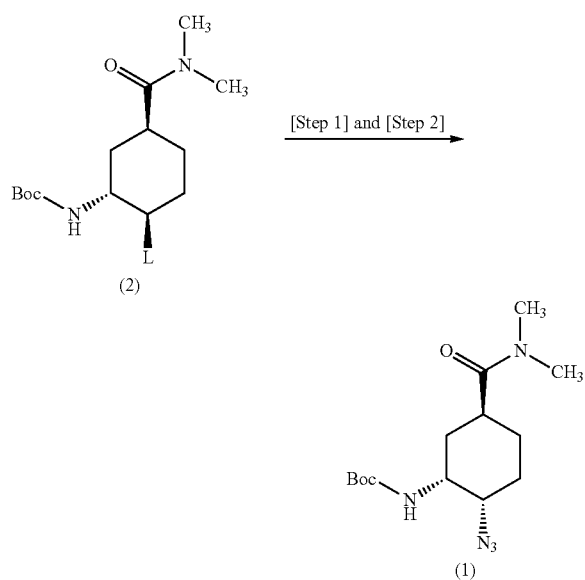

wherein Boc and L are as defined above.

The production method of the present invention comprises:

[Step 1]: adding a quaternary ammonium salt and a metal azide salt to water to prepare an aqueous solution of an azidification reagent complex comprising quaternary ammonium salt-metal azide salt, and subsequently dehydrating the aqueous solution using an aromatic hydrocarbon solvent to form a mixed solution of the azidification reagent complex comprising quaternary ammonium salt-metal azide salt and the aromatic hydrocarbon solvent with a water content of 0.2% or less; and

[Step 2]: adding, to the mixed solution prepared in [Step 1], a compound (2):

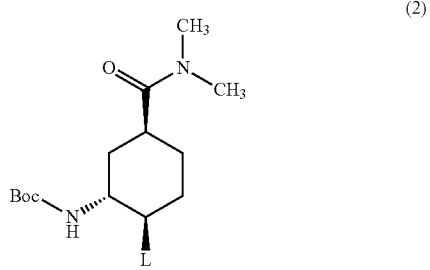

After the completion of the reaction, the reaction mixture of [Step 2] is treated with an aqueous alkali solution as a usual work-up procedure, followed by extraction with an aromatic hydrocarbon solvent and washing of the extracts with water to obtain compound (1).

The leaving group represented by L in compound (2) according to the present invention is preferably a (C1 to C2 alkyl)sulfonyloxy group (wherein the C1 to C2 alkyl group may have one or more identical or different halogeno groups as substituents) and a benzenesulfonyloxy group (wherein the benzene ring may have one or more identical or different groups as substituents selected from a halogeno group, a methyl group, and a nitro group), more preferably a methanesulfonyloxy, ethanesulfonyloxy, trifluoromethanesulfonyloxy, 2-chloroethanesulfonyloxy, benzenesulfonyloxy, p-toluenesulfonyloxy, 4-chlorobenzenesulfonyloxy, 2-chlorobenzenesulfonyloxy, 4-nitrobenzenesulfonyloxy, or 2-nitrobenzenesulfonyloxy group.

L is even more preferably a methanesulfonyloxy or ethanesulfonyloxy group, particularly preferably a methanesulfonyloxy group.

Preferable examples of the quaternary ammonium salt according to the present invention can include quaternary ammonium salts of alkylamines, and pyridinium salts. In this context, examples of the quaternary ammonium salts of alkylamines include tetramethylammonium chloride, tetrabutylammonium chloride, trioctylmethylammonium chloride, benzyltrimethylammonium chloride, and benzyltributylammonium chloride, and those in which chloride ions in these salts are substituted by other anions (e.g., bromide, iodide, and bisulfate ions). Examples of the pyridinium salts can include: N-alkylpyridinium chlorides such as N-butylpyridinium chloride, N-hexylpyridinium chloride, N-octylpyridinium chloride, N-dodecylpyridinium chloride (N-laurylpyridinium chloride), and N-cetylpyridinium chloride; N-alkylpicolinium chlorides such as N-lauryl-2-picolinium chloride, N-cetyl-2-picolinium chloride, N-lauryl-3-picolinium chloride, N-cetyl-3-picolinium chloride, N-lauryl-4-picolinium chloride, and N-cetyl-4-picolinium chloride; N-alkyl-4-phenylpropylpyridinium chlorides such as N-butyl-4-phenylpropylpyridinium chloride, N-hexyl-4-phenylpropylpyridinium chloride, N-octyl-4-phenylpropylpyridinium chloride, and N-lauryl-4-phenylpropylpyridinium chloride; and those in which chloride ions in these salts are substituted by other anions (e.g., bromide, iodide, and bisulfate ions).

The quaternary ammonium salt according to the present invention is preferably a pyridinium salt, more preferably a 1-(C4 to C20 alkyl)pyridinium salt.

The 1-(C4 to C20 alkyl)pyridinium salt is preferably a 1-dodecylpyridinium salt, more preferably a 1-(C4 to C20 alkyl)pyridinium halide, particularly preferably 1-dodecylpyridinium chloride (also known as 1-laurylpyridinium chloride).

The amount of the quaternary ammonium salt used in [Step 1] of the present invention is preferably 0.45 to 0.55 molar equivalent with respect to compound (2). The quaternary ammonium salt can be used in an amount of 0.55 molar equivalent or more with respect to compound (2). Since the quaternary ammonium salt is a phase-transfer catalyst, a possible loss may occur during extraction procedures. Thus, the amount of the quaternary ammonium salt used is more preferably approximately 0.5 molar equivalent with respect to compound (2).

The metal azide salt used in [Step 1] of the present invention is preferably an alkali metal azide salt, more preferably sodium azide or lithium azide, particularly preferably sodium azide.

The amount of the metal azide salt used is preferably in the range of 1.8 to 2.2 molar equivalents, more preferably approximately 2.0 molar equivalents, with respect to compound (2), though the amount is not limited to this range in any way.

The amount of water used for preparing an azidification reagent complex from the quaternary ammonium salt and the metal azide salt is preferably in the range of 1 to 2 parts by volume [1 to 2 (v/w)], more preferably approximately 1.0 part by volume [1.0 (v/w)], with respect to 1 part by weight of the compound (2), though the amount is not limited to this range in any way. Water used as a solvent is preferably used in a small amount for removing it by the subsequent azeotropic dehydration procedure, as long as it does not impair the preparation of the azidification reagent complex.

The temperature for preparing the azidification reagent complex in [Step 1] may be room temperature and is preferably in the range of 20 to 40° C. The stirring time for preparing the azidification reagent complex in [Step 1] is preferably 0.5 hour or longer, more preferably in the range of 0.5 to 1.5 hours, though the stirring time is not limited to this range in any way.

Dehydration in [Step 1] means azeotropic dehydration using an organic solvent for azeotropy of water and is preferably azeotropic dehydration using an aromatic hydrocarbon solvent.

Dehydration in the present invention means azeotropic dehydration using an organic solvent known for azeotropy of water and is preferably azeotropic dehydration under heating using an aromatic hydrocarbon solvent. In the azeotropic dehydration, water removal apparatus may be used. Examples of water removal apparatus can include, but are not limited to in any way, a Dean-Stark water trap.

The azeotropic dehydration in the present invention can be performed by removing water in the mixed solution of the aqueous solution of the azidification reagent complex and the aromatic hydrocarbon solvent by azeotropy and may be performed by gradually adding dropwise the aqueous solution of the azidification reagent complex to the aromatic hydrocarbon solvent under heating.

In this context, the temperature for performing the azeotropic dehydration must be a temperature equal to or higher than the boiling point of the aromatic hydrocarbon solvent used, under normal pressure. In the azeotropic dehydration, a high-boiling solvent generally offers a high dehydration effect but however, requires preventing decomposition of the prepared azidification reagent complex. Alternatively, azeotropic dehydration under reduced pressure can be carried out at a temperature equal to or lower than the boiling point of the aromatic hydrocarbon solvent used. Since the prepared azidification reagent complex is a mixture of salts, this is preferred to prevent soap-like foaming in the organic solvent. The aromatic hydrocarbon solvent is distilled off together with water by this azeotropic dehydration, decreasing the solvent in the reaction system. However, the reaction system can be replenished appropriately with aromatic hydrocarbon solvent.

The aromatic hydrocarbon solvent according to the present invention is preferably benzene, toluene, xylene, chlorobenzene, or dichlorobenzene. These solvents may be used alone (one thereof) or as a mixed solvent in which two or more thereof are mixed. The aromatic hydrocarbon solvent is more preferably toluene.

The amount of the aromatic hydrocarbon solvent used is preferably approximately 5 parts by volume with respect to 1 part by weight of compound (2) [5 (v/w)], though the amount is not limited thereto in any way. In [Step 1], the water content is preferably set to 0.2% or less, more preferably 0.1% or less.

The azeotropic dehydration in [Step 1] is preferably performed by gradually adding dropwise the aqueous solution of the azidification reagent complex to the aromatic hydrocarbon solvent under heating, more preferably under reduced pressure, for preventing foaming.

Hereinafter, a preferred embodiment of [Step 1] in the present invention will be described.

A quaternary ammonium salt at 0.5 molar equivalent with respect to compound (2) and a metal azide salt at 2 molar equivalents with respect to compound (2) are added to water at 1 part by volume with respect to 1 part by weight of compound (2) [1 (v/w)], and the mixture is stirred for 1 hour to prepare an aqueous solution of an azidification reagent complex.

Subsequently, the aqueous solution of the azidification reagent complex is added dropwise, with care to avoid foaming, into toluene at 5 parts by volume with respect to 1 part by weight of compound (2) [5 (v/w)] (toluene is heated in advance to an internal temperature of 40 to 60° C.). Water is dehydrated by azeotropy under reduced pressure.

In the azeotropic dehydration, a Dean-Stark water trap or the like may be used appropriately.

After completion of the dropwise addition of the aqueous solution of the azidification reagent complex, the water content in the mixed solution is confirmed to be 0.2% or less, preferably 0.1% or less, and then, toluene is added thereto at 5 parts by volume with respect to 1 part by weight of compound (2) [5 (v/w)].

The thus-prepared mixed solution of the azidification reagent complex and the aromatic hydrocarbon solvent with a water content of 0.2% or less has been confirmed to have a small risk of explosion.

[Step 2] in the present invention is the step of adding a compound represented by the following formula (2):

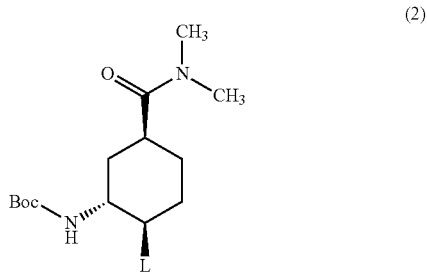

wherein L and Boc are as defined above,
to the mixed solution prepared in [Step 1] and treating the mixture under heating.

The temperature and the stirring time in [Step 2] are preferably 69 to 71° C. in terms of the internal temperature of the reaction mixture and within 18 hours.

The conventional method requires adjusting the reaction temperature to 60 to 63° C. in terms of the internal temperature, for preventing compound (2) from being decomposed due to water in the reaction solvent. However, at this temperature, approximately 36 hours are necessary as a reaction time.

In the present invention, it was demonstrated that even at a reaction temperature raised to 69 to 71° C. in terms of the internal temperature, decomposition of compound (2) can be prevented by adjusting the water content in the mixed solution of the azidification reagent complex and the aromatic hydrocarbon solvent to 0.2% or less, more preferably 0.1% or less.

The criterion for determining the endpoint of the reaction is preferably a compound (2) residual rate of 2% or less in terms of an area ratio obtained using HPLC.

The work-up procedure after completion of the reaction in the present invention is preferably an aqueous alkali solution treatment of the mixed solution obtained in [Step 2].

The aqueous alkali solution according to the present invention means an aqueous solution of the hydroxide, carbonate, or bicarbonate, or the like of an alkali metal or an alkaline earth metal. Any of these aqueous alkali solutions can be used as saturated aqueous solutions or at lower concentrations as long as they neither decompose products or the like nor impair procedures such as extraction procedures. The aqueous alkali solution according to the present invention is preferably an aqueous sodium hydroxide solution, an aqueous potassium hydroxide solution, an aqueous sodium carbonate solution, an aqueous potassium carbonate solution, an aqueous sodium bicarbonate solution, or an aqueous potassium bicarbonate solution, more preferably an aqueous sodium bicarbonate solution or an aqueous potassium bicarbonate solution.

After completion of [Step 2] in the present invention, the reaction mixture is preferably allowed to cool and washed with an aqueous alkali solution, followed by extraction with an aromatic hydrocarbon solvent under heating. In this context, the phrase "allowed to cool" means that the reaction solution after completion of the reaction is cooled to room temperature in terms of its internal temperature. The aqueous alkali solution exemplified above can be used as the aqueous alkali solution. Preferable examples of the aqueous alkali solution can include 5% aqueous bicarbonate solutions. The amount of the aqueous alkali solution used is preferably 5 parts by volume with respect to 1 part by weight of compound (2) [5 (v/w)]. The washing is performed by adding the aqueous alkali solution thereto, then stirring the mixed solution, and separating the aqueous layer as the lower layer by still standing. The extraction with toluene under heating is the procedure of adding toluene to the separated aqueous layer and separating the toluene layer as the upper layer. This extraction procedure may be repeated. The heating temperature in the extraction procedure is preferably approximately 40° C. The amount of toluene used in the extraction is preferably approximately 2 parts by volume with respect to 1 part by weight of compound (2) [2 (v/w)]. The layer separated by the previous washing with the alkali solution and the extracted toluene layer are combined and used as toluene extracts of compound (2).

The toluene extracts can be washed with water to prepare a solution of compound (1) in the aromatic hydrocarbon solvent. In this context, the amount of water used in the washing with water is preferably approximately 1.5 parts by volume with respect to 1 part by weight of compound (2) [1.5 (v/w)]. The washing temperature with water is preferably approximately 40° C. The toluene layer is separated and used as a solution of compound (1) in toluene.

Compound (2a) wherein the leaving group L in compound (2) used in [Step 2] is a methanesulfonyloxy group can be produced, for example, as shown in [Scheme 1] shown below. Specific examples of the production can include a method described in Reference Example 1.

Specifically, compound (2a) can be produced by producing a compound (6) from a compound (5) and methanesulfonylating this compound (6). Compound (5) can be produced by a method described in WO 2007/032498.

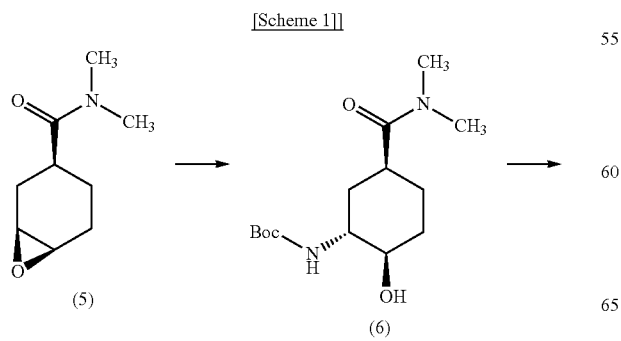

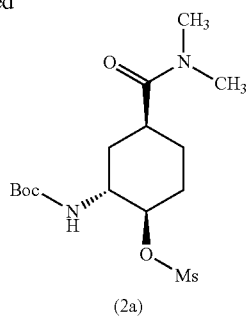

wherein Boc and Ms are as defined above.

The present invention also provides a method for producing a compound (4) represented by the following formula:

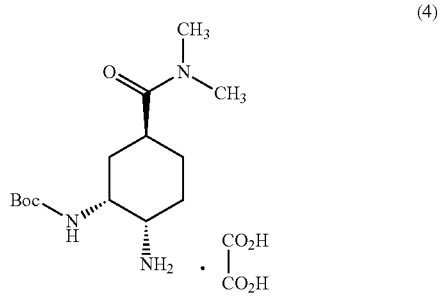

wherein Boc is as defined above,
the method comprising the steps of:
concentrating the aromatic hydrocarbon solvent in the solvent solution of compound (1) represented by the following formula:

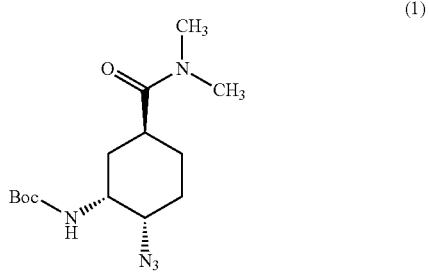 [SMILES: CN(C)C(=O)[C@H]1CC[C@H](N=[N+]=[N-])[C@H](NC(=O)OC(C)(C)C)C1]

wherein Boc is as defined above,
obtained in the present invention, dissolving the obtained residue in an alcohol solvent, and then performing a reduction reaction of the azide group to obtain a compound (3) represented by the following formula or a salt thereof, or a solvate thereof:

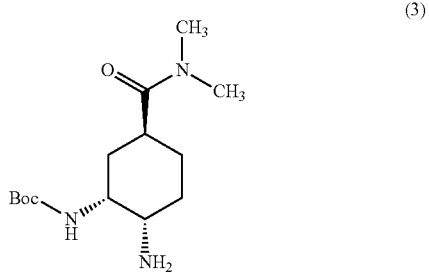 [SMILES: CN(C)C(=O)[C@H]1CC[C@H](N)[C@H](NC(=O)OC(C)(C)C)C1]

wherein Boc is as defined above; and
treating compound (3) or the salt thereof, or the solvate thereof with oxalic acid to obtain compound (4).

Examples of methods for producing an FXa inhibitor (A-a) in the same way as in the production methods disclosed in Patent Literature 1 or 3 using compound (1) of the present invention can include methods shown in the following schemes and Reference Examples:
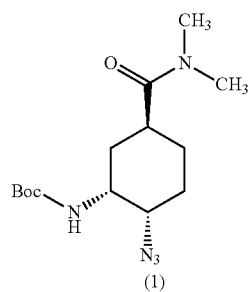
(1)
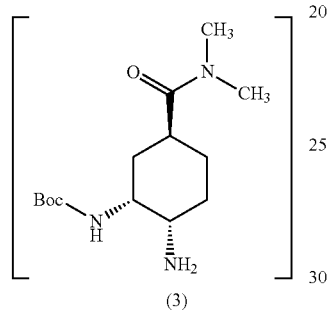
(3)
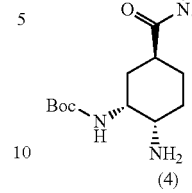
(4)
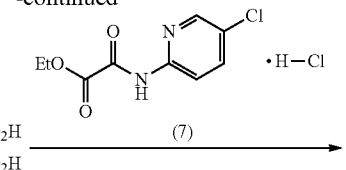
(7)
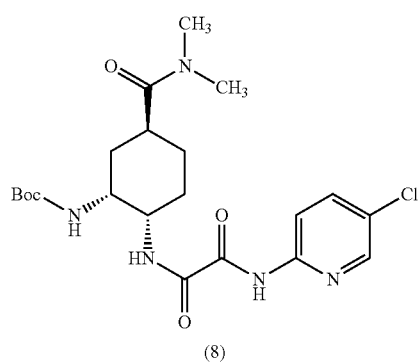
(8)
wherein Boc is as defined above.
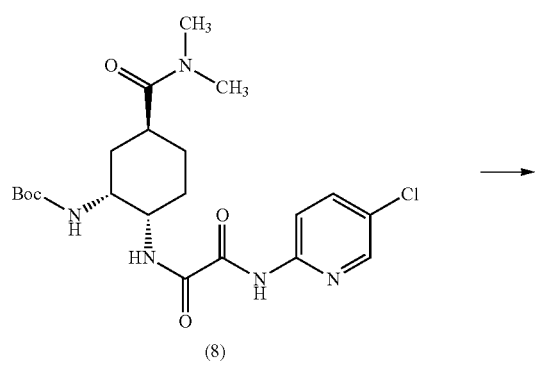
(8)
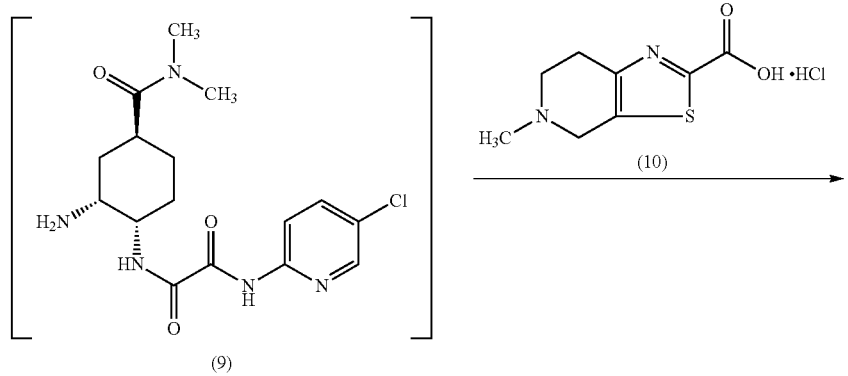
(9)
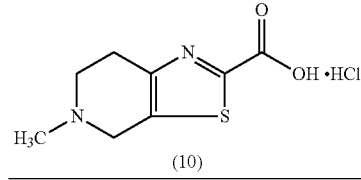
(10)

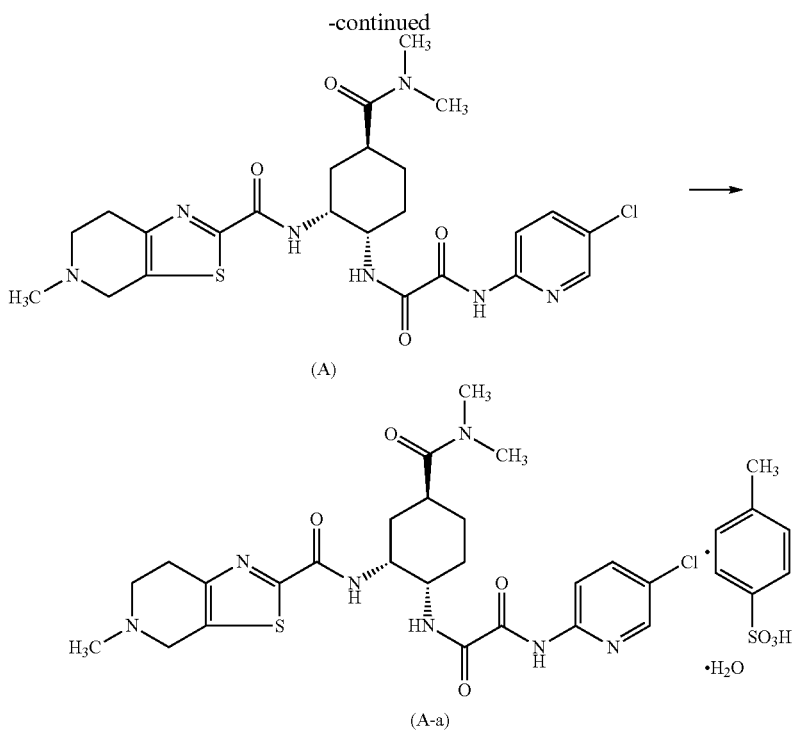

wherein Boc is as defined above.

EXAMPLES

Next, the present invention will be described in detail with reference to the Reference Examples and Examples. However, the present invention is not intended to be limited to these in any way.

Tetramethylsilane was used as the internal standard for the nuclear magnetic resonance (NMR) spectra. Abbreviations showing multiplicity represent s=singlet, d=doublet, t=triplet, q=quartet, m=multiplet, and brs=broad singlet.

Reference Example 1

(1R,2R,4S)-2-[(tert-butoxycarbonyl)amino]-4-[(dimethylamino)carbonyl]cyclohexylmethanesulfonate (2a)

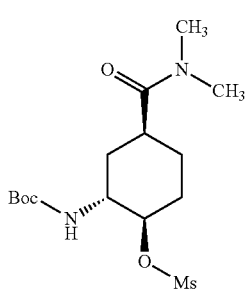

wherein Boc represents a tert-butoxycarbonyl group; and Ms represents a methanesulfonyl group.

[Step 1] Synthesis of tert-butyl {(1R,2R,5S)-5-[(dimethylamino)carbonyl]-2-hydroxycyclohexyl}carbamate (6)

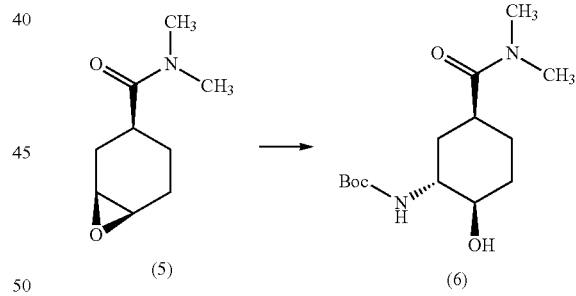

wherein Boc is as defined above.

A 28% aqueous ammonia solution (5 ml) was added to (1S,3S,6R)—N,N-dimethyl-7-oxabicyclo[4.1.0]heptane-3-carboxamide (5) (1 g) at room temperature. The mixed solution was stirred at 40° C. for hours, and then, the solvent was concentrated under reduced pressure to obtain (1S,3R,4R)-3-amino-4-hydroxy-N,N-dimethylcyclohexanecarboxamide (1.18 g).

The obtained (1S,3R,4R)-3-amino-4-hydroxy-N,N-dimethylcyclohexanecarboxamide (1.18 g) was dissolved in water (5 ml). To the solution, di-tert-butyl dicarbonate (1.93 g) and a 10 N aqueous sodium hydroxide solution (1.5 ml) were then added at room temperature. The reaction mixture was stirred at 40° C. for 2 hours and then subjected to extraction with 4-methyl-2-pentanone (MIBK) (5 ml) three times, and the solvent in the extracts was distilled off under reduced pressure. To the residue, 4-methyl-2-pentanone (MIBK) (3 ml) was added, and the mixture was stirred at room temperature. The precipitated crystals were collected by filtration and dried to obtain the title compound (6) (1.26 g).

$^1$H-NMR (CDCl$_3$) δ: 1.44 (9H, s), 1.48-1.59 (2H, m), 1.77-1.78 (2H, m), 1.86-1.97 (1H, m), 2.11-2.17 (1H, m), 2.78-2.83 (1H, m), 2.92 (3H, s), 3.02 (3H, s), 3.53-3.60 (1H, m), 3.94 (1H, br.s), 4.52-4.68 (1H, m).

[Step 2] Synthesis of (1R,2R,4S)-2-[(tert-butoxycarbonyl)amino]-4-[(dimethylamino)carbonyl]cyclohexylmethanesulfonate (2a)

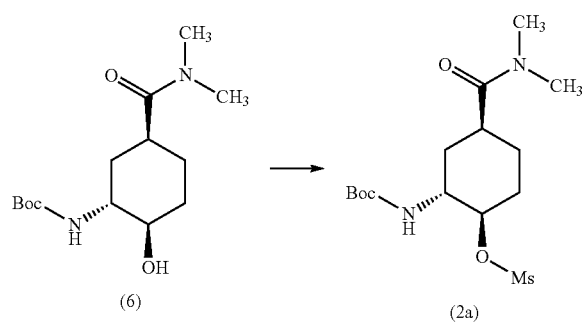 [SMILES: CN(C)C(=O)[C@H]1CC[C@@H](O)[C@H](NC(=O)OC(C)(C)C)C1 ; CN(C)C(=O)[C@H]1CC[C@@H](OS(C)(=O)=O)[C@H](NC(=O)OC(C)(C)C)C1]

wherein Boc and Ms are as defined above.

Methanesulfonyl chloride (159.07 g) was added to a solution of tert-butyl {(1R,2R,5S)-5-[(dimethylamino)carbonyl]-2-hydroxycyclohexyl}carbamate (6) (214.59 g) in 4-methyl-2-pentanone (MIBK) (1875 ml) with stirring at room temperature. To the mixed solution, triethylamine (170.62 g) was added at room temperature, and the mixture was stirred at this temperature for 1 hour. To the reaction solution, water was added, and then, the organic layer was separated. The solvent was concentrated under reduced pressure. To the concentrated residue, MIBK (750 ml) was then added, and the mixture was stirred at room temperature for 3 hours. The precipitated crystals were collected by filtration and dried to obtain the title compound (2a) (242.57 g).

$^1$H-NMR (CDCl$_3$) δ: 1.45 (9H, s), 1.58-1.66 (1H, m), 1.67-1.76 (1H, m), 1.84-1.96 (2H, m), 2.04-2.15 (1H, m), 2.17-2.26 (1H, m), 2.75-2.81 (1H, m), 2.94 (3H, s), 3.04 (3H, s), 3.07 (3H, s), 4.00-4.08 (1H, m), 4.69-4.82 (2H, m).

Reference Example 2

Tert-butyl {(1R,2R,5S)-2-azido-5-[(dimethylamino)carbonyl]cyclohexyl}carbamate (1) (production method of WO 2007/032498)

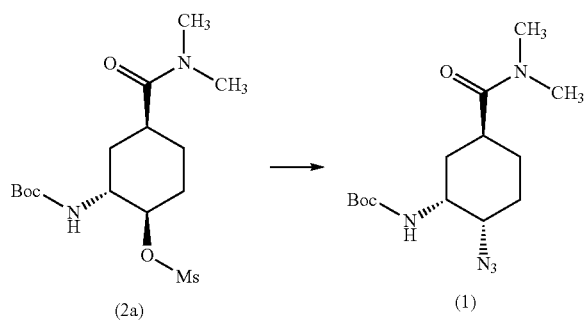 [SMILES: CN(C)C(=O)[C@H]1CC[C@@H](OS(C)(=O)=O)[C@H](NC(=O)OC(C)(C)C)C1 ; CN(C)C(=O)[C@H]1CC[C@H](N=[N+]=[N-])[C@H](NC(=O)OC(C)(C)C)C1]

wherein Boc and Ms are as defined above.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (2a) (20.0 g) in N,N-dimethylacetamide (DMAC) (40 ml) at room temperature. The mixed solution was stirred at 60° C. for 72 hours and then allowed to cool to room temperature. To the reaction solution, water was added, followed by extraction with ethyl acetate. The extracts were washed with a saturated aqueous solution of sodium bicarbonate and water, and then, the solvent was concentrated under reduced pressure. To the concentrated residue, an n-hexane-ethyl acetate (5:1) mixed solvent (300 ml) was added, and the mixture was stirred at room temperature for 1 hour. The precipitated crystals were collected by filtration. The procedure of adding an n-hexane-ethyl acetate (5:1) mixed solvent (300 ml) to the obtained crystals, followed by stirring and crystal collection by filtration was repeated twice to obtain the title compound (1) (4.6 g, 26.9%).

$^1$H-NMR (CDCl$_3$) δ: 1.46 (9H, s), 1.55-1.74 (3H, m), 1.75-1.82 (1H, m), 2.02-2.12 (2H, m), 2.74-2.83 (1H, m), 2.93 (3H, s), 3.02 (3H, s), 3.72-3.78 (1H, m), 4.07-4.13 (1H, m), 4.61-4.66 (1H, m).

Reference Example 3

Tert-butyl {(1R,2S,5S)-2-amino-5-[(dimethylamino)carbonyl]cyclohexyl}carbamate oxalate (4)

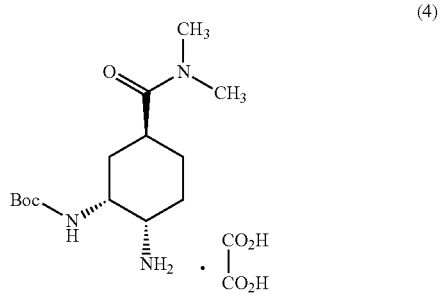

wherein Boc is as defined above.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (2a) (20.0 g) in toluene (100 ml) at room temperature. The mixed solution was stirred at 60° C. for 72 hours and then allowed to cool to room temperature. To the reaction solution, water was added, and the organic layer was separated. The organic layer was washed with a saturated aqueous solution of sodium bicarbonate and water, and then, the solvent was distilled off. To the residue, methanol, and then 7.5% Pd—C and ammonium formate were added, and the mixture was stirred at 40° C. for 1 hour. Pd—C was filtered off, and then, the solvent was concentrated under reduced pressure. To this residue, aqueous acetonitrile (200 ml) and anhydrous oxalic acid (4.94 g) were added, and the mixture was stirred at room temperature for 17 hours. The precipitated crystals were collected by filtration. The obtained crystals were added to acetonitrile (200 ml), and the mixture was stirred at 40° C. for 24 hours. The precipitated crystals were collected by filtration and dried to obtain the title compound (4) (12.7 g).

¹H-NMR (D₂O) δ: 1.30 (9H, s), 1.37-1.49 (2H, m), 1.63 (1H, t, J=2.7 Hz), 1.72-1.83 (3H, m), 2.77 (3H, s) 2.80 (1H, t, J=12.4 Hz), 2.96 (3H, m), 3.32 (1H, d, J=12.2 Hz), 4.10 (1H, br).

Anal.: C₁₆H₂₉N₃O₇.
Theoretical: C, 50.70%; H, 7.75%; N, 10.96%.
Found: C, 51.19%; H, 7.79%; N, 11.19%.

Reference Example 4

2-[(5-chloropyridin-2-yl)amino]-2-oxoacetate monohydrochloride (7)

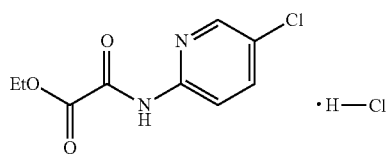

Ethyl oxalyl chloride (11.7 g) was added to a suspension of 2-amino-5-chloropyridine (10.0 g) in acetonitrile (120 ml) at 50° C., and the mixture was stirred at this temperature for 2 hours. The reaction solution was cooled, and crystals were collected by filtration at 10° C., washed with acetonitrile (40 ml), and then dried under reduced pressure to obtain the title compound (7) (19.7 g).

Reference Example 5

Tert-butyl (1R,2S,5S)-2-({2-[(5-chloropyridin-2-yl)amino]-2-oxoacetyl}amino)-5-(dimethylaminocarbonyl)cyclohexylcarbamate (8)

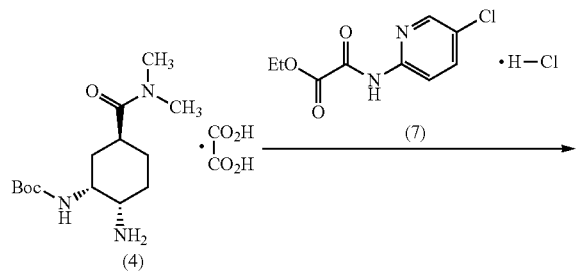

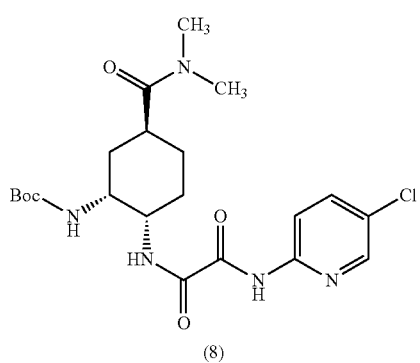

wherein Boc is as defined above.

Triethylamine (169 ml) was added to a suspension of tert-butyl (1R,2S,5S)-2-amino-5-(dimethylaminocarbonyl)cyclohexylcarbamate monooxalate (4) (100.1 g) in acetonitrile (550 ml) at 60° C. 2-[(5-chloropyridin-2-yl)amino]-2-oxoacetate monohydrochloride (7) (84.2 g) was added thereto at this temperature, and the mixture was stirred for 6 hours and then stirred at room temperature for 16 hours. To the reaction solution, water was added, and the mixture was stirred at 10° C. for 1.5 hours. Then, crystals were collected by filtration to obtain the title compound (8) (106.6 g).

¹H-NMR (CDCl₃) δ: 1.25-1.55 (2H, m), 1.45 (9H, s), 1.60-2.15 (5H, m), 2.56-2.74 (1H, br.s), 2.95 (3H, s), 3.06 (3H, s), 3.90-4.01 (1H, m), 4.18-4.27 (1H, m), 4.70-4.85 (0.7H, br), 5.70-6.00 (0.3H, br.s), 7.70 (1H, dd, J=8.8, 2.4 Hz), 7.75-8.00 (1H, br), 8.16 (1H, br.d, J=8.8 Hz), 8.30 (1H, d, J=2.4 Hz), 9.73 (1H, s).

Reference Example 6

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (A)

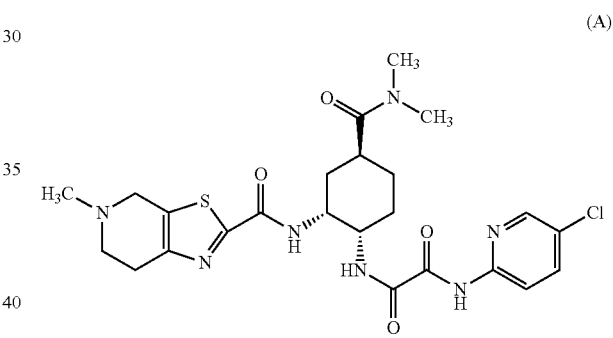

Methanesulfonic acid (66 ml) was added to a suspension of tert-butyl [(1R,2S,5S)-2-({[(5-chloropyridin-2-yl)amino](oxo)acetyl}amino)-5-(dimethylaminocarbonyl)cyclohexyl]carbamate (8) (95.1 g) in acetonitrile (1900 ml) at room temperature, and the mixture was stirred at this temperature for 2 hours. To the reaction solution, triethylamine (155 ml), 5-methyl-4,5,6,7-tetrahydro[1,3]thiazolo[5,4-c]pyridine-2-carboxylic acid hydrochloride (10) (52.5 g), 1-hydroxybenzotriazole (33.0 g), and 1-ethyl-3-(3-dimethylaminopropyl)carbodiimide hydrochloride (46.8 g) were added under ice cooling, and the mixture was stirred at room temperature for 16 hours. Triethylamine and water were added thereto, and the mixture was stirred for 1 hour under ice cooling. Then, crystals were collected by filtration to obtain the title compound (A) (103.2 g).

¹H-NMR (CDCl₃) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, dd, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s).

MS (ESI) m/z: 548 (M+H)⁺.

Reference Example 7

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (A-a)

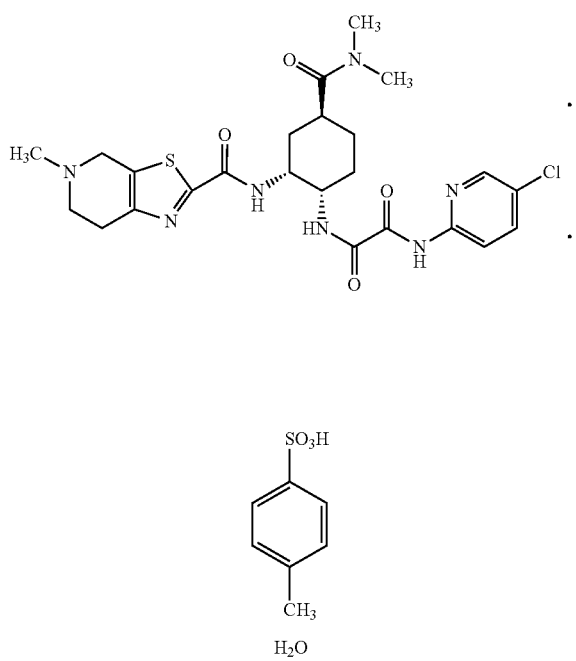

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (A) (6.2 g) was dissolved in methylene chloride (120 ml). To the solution, a 1 mol/L solution of p-toluenesulfonic acid in ethanol (11.28 ml) was added, and the solvent was distilled off. To the residue, 15% hydrous ethanol (95 ml) was added, and the mixture was dissolved by stirring at 60° C. Then, the mixture was cooled to room temperature and stirred for 1 day. The precipitated crystals were collected by filtration, washed with ethanol, and then dried under reduced pressure at room temperature for 2 hours to obtain the title compound (A-a) (7.4 g).

$^1$H-NMR (DMSO-d$_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br), 10.18 (1H, br), 10.29 (1H, s).

MS (ESI) m/z: 548 (M+H)$^+$.

Anal.: C$_{24}$H$_{30}$ClN$_7$O$_4$S·C$_7$H$_8$O$_3$S·H$_2$O

Theoretical: C, 50.43; H, 5.46; N, 13.28; Cl, 4.80; S, 8.69.

Found: C, 50.25; H, 5.36; N, 13.32; Cl, 4.93; S, 8.79.

mp (dec.): 245-248° C.

Example 1

Tert-butyl {(1R,2R,5S)-2-azido-5-[(dimethylamino)carbonyl]cyclohexyl}carbamate (1)

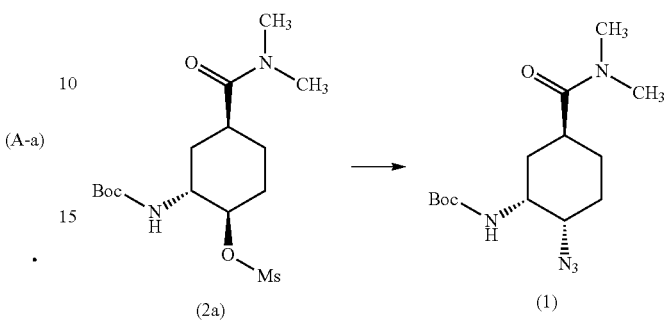

wherein Boc is as defined above.

Sodium azide (32.82 g) [2 molar equivalents with respect to compound (2a)] and dodecylpyridinium chloride (DPC) (35.83 g) [0.5 molar equivalent with respect to compound (2a)] were added to water (92 ml) [1 part by volume (v/w) with respect to compound (2a)]. Dissolution was confirmed, and then, the mixture was stirred for approximately 1 hour. Toluene (460 ml) [5 parts by volume (v/w) with respect to compound (2a)] was placed in a flask, and an aqueous solution of the azidification reagent complex prepared from sodium azide and dodecylpyridinium chloride (DPC) was gradually added dropwise thereto under reflux under reduced pressure (internal temperature: approximately 40 to 60° C.) with care to avoid foaming. At the same time, water was separated and removed from the distillate using a Dean-Stark apparatus. Several hours after completion of the dropwise addition, the toluene solution was confirmed to have a water content of 0.1% or less, and then, the reduced pressure was cancelled. (1R,2R,4S)-2-[(tert-butoxycarbonyl)amino]-4-[(dimethylamino)carbonyl]cyclohexylmethanesulfonate (2a) (92 g) was added thereto, and the mixture was stirred at an internal temperature of 70° C. for approximately 18 hours. A residue of 2% or less of compound (2a) was confirmed, and then, the reaction mixture was cooled. A 5% aqueous NaHCO$_3$ solution (460 ml) [5 parts by volume (v/w) with respect to compound (2a)] was added thereto, and the mixture was separated into organic and aqueous layers by stirring at an internal temperature of approximately 40° C., extraction, and still standing. To the separated aqueous layer, toluene (184 ml) [2 parts by volume (v/w) with respect to compound (2a)] was added, followed by re-extraction at an internal temperature of approximately 40° C. (this was repeated to a total of three times). These toluene layers were mixed, and water (138 ml) [1.5 times (v/w) with respect to compound (2a)] was added thereto, followed by washing with water at an internal temperature of approximately 40° C. (this was repeated to a total of twice) to obtain a solution of the title compound in toluene (yield: 71 to 75%).

Test Example 1

(Condition 1) to (Condition 7) shown below were studied as conditions for producing compound (1) from compound (2a). Results of examining the loss of compound (1) during extraction after completion of the reaction under each of (Condition 1) to (Condition 7) and the yield of compound (1) are shown in Table 1.

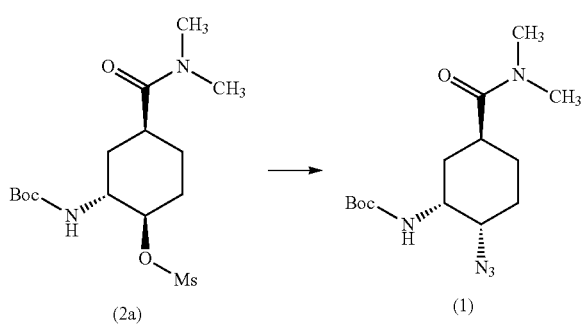 [SMILES: CN(C)C(=O)[C@H]1CC[C@@H](OS(C)(=O)=O)[C@H](NC(=O)OC(C)(C)C)C1 ; CN(C)C(=O)[C@H]1CC[C@H](N=[N+]=[N-])[C@H](NC(=O)OC(C)(C)C)C1]

wherein Boc and Ms are as defined above.

Condition 1

Comparative Example

The optimized condition of the conventional method (WO 2007/032498) free from water adjustment. Sodium azide [2 molar equivalent with respect to compound (2a)] and dodecylpyridinium chloride [0.5 molar equivalent with respect to compound (2a)] were suspended in toluene (5 parts by volume with respect to compound (2a)), and this suspension was stirred at 60° C. for 24 hours. Then, compound (2a) was added thereto, and the mixture was stirred at 60 to 63° C. for 60 to 72 hours.

Condition 2

Example 2

Sodium azide (2 molar equivalent) and dodecylpyridinium chloride (0.5 molar equivalent) were dissolved in water (1 v/w), and the solution was stirred at 60° C. for 30 minutes. Then, toluene was added thereto, and the water content of the mixed solution was adjusted to 0.03% by azeotropic dehydration procedures using a Dean-Stark water trap. Additional toluene was added to adjust the amount of toluene in the mixed solution to (5 v/w). Then, compound (2a) was added thereto, and the mixture was stirred at 60 to 63° C. for 47 hours. The numeric value within the parentheses represents the amount with respect to compound (2a).

Condition 3

Example 3

Sodium azide (2 molar equivalent) and dodecylpyridinium chloride (0.75 molar equivalent) were dissolved in water (1 v/w), and the solution was stirred at 60° C. for 1 hour. Then, toluene was added thereto, and the water content of the mixed solution was adjusted to 0.12% by azeotropic dehydration procedures using a Dean-Stark water trap. Additional toluene was added to adjust the amount of toluene in the mixed solution to (5 v/w). Then, compound (2a) was added thereto, and the mixture was stirred at 60 to 63° C. for 22.5 hours. The numeric value within the parentheses represents the amount with respect to compound (2a).

Condition 4

Comparative Example

Sodium azide (2 molar equivalent) and dodecylpyridinium chloride (0.5 molar equivalent) were suspended in toluene (5 v/w), and the suspension was stirred at 60° C. for 1 hour. Then, the water content of the mixed solution was adjusted to 0.023% by azeotropic dehydration procedures using a Dean-Stark water trap. Additional toluene was added to adjust the amount of toluene in the mixed solution to (5 v/w). Then, compound (2a) was added thereto, and the mixture was stirred at 60 to 63° C. for 45 hours. The numeric value within the parentheses represents the amount with respect to compound (2a).

Condition 5

Comparative Example

Sodium azide (2 molar equivalent) and dodecylpyridinium chloride (0.5 molar equivalent) were suspended in toluene (5 v/w), and the suspension was stirred at 60° C. for 1 hour. Then, the water content of the mixed solution was adjusted to 0.052% by azeotropic dehydration procedures using a Dean-Stark water trap. Additional toluene was added to adjust the amount of toluene in the mixed solution to (5 v/w). Then, compound (2a) (150 g, scale-up experiment) was added thereto, and the mixture was stirred at 60 to 63° C. for 63 hours. The numeric value within the parentheses represents the amount with respect to compound (2a).

Condition 6

Example 4

Sodium azide (2 molar equivalent) and dodecylpyridinium chloride (0.5 molar equivalent) were dissolved in water (2 v/w), and the solution was stirred at 60° C. for 3 hours. Then, toluene was added thereto, and the water content of the mixed solution was adjusted to 0.062% by azeotropic dehydration procedures using a Dean-Stark water trap. Additional toluene was added to adjust the amount of toluene in the mixed solution to (5 v/w). Then, compound (2a) (100-g, scale-up experiment) was added thereto, and the mixture was stirred at 60 to 63° C. for 35 hours. The numeric value within the parentheses represents the amount with respect to compound (2a).

Condition 7

Comparative Example

Dodecylpyridinium chloride (0.5 molar equivalent) was suspended in toluene (5 v/w). Then, the water content of the mixed solution was adjusted to 0.033% by azeotropic dehydration procedures using a Dean-Stark water trap. Additional toluene was added to adjust the amount of toluene in the mixed solution to (5 v/w). Sodium azide (2 molar equivalent) was added thereto, and the mixture was stirred at 60° C. for 1 hour. Compound (2a) was added thereto, and the mixture was stirred at 60 to 63° C. for 60 hours. The numeric value within the parentheses represents molar equivalents, parts by weight, or parts by volume amount with respect to compound (2a).

TABLE 1

| Condition | Loss during extraction | Yield of compound (1) |
| --- | --- | --- |
| 1 (Comparative Example) | 2~4% | 60~65% |
| 2 (Example 2) | 1.6% | 76.7% |
| 3 (Example 3) | 4.7% | 72.6% |

TABLE 1-continued

| Condition | Loss during extraction | Yield of compound (1) |
|---|---|---|
| 4 (Comparative Example) | 3.12% | 74.1% |
| 5 (Comparative Example) | — | 64.2% |
| 6 (Example 4) | 2.34% | 73.5% |
| 7 (Comparative Example) | 2.88% | 46.9% |

<Test Results>

Improved yields and a reduced reaction time were observed by distilling off water in dodecylpyridinium chloride (Condition 1 vs. Condition 2). Moreover, the increased amount of dodecylpyridinium chloride used did not contribute to an improvement in yield, due to a larger loss into the aqueous layer during separation into organic and aqueous layers, although a reduction in reaction time was observed (comparison between Conditions 3 and 2). The importance of the procedure of stirring dodecylpyridinium chloride and sodium azide in water was studied (comparison among Conditions 4, 5, and 6). In the small-scale experiment, the yield equivalent to that obtained using water as a solvent was obtained even using a suspension in toluene (Condition 4). By contrast, the yield was reduced due to scale-up (Condition 5). This demonstrated the importance of the procedure of stirring dodecylpyridinium chloride and sodium azide in an aqueous solution (Condition 6). Thus, reaction in water is suitable for large-scale production. Dehydration under Condition 7 using only dodecylpyridinium chloride increased impurities and reduced yields.

INDUSTRIAL APPLICABILITY

The production method of the present invention can be used as a novel method for industrially producing compound (A) useful as an FXa inhibitor or a pharmacologically acceptable salt thereof, or a hydrate thereof.

The invention claimed is:

1. A method for producing a compound (1) represented by the following formula:

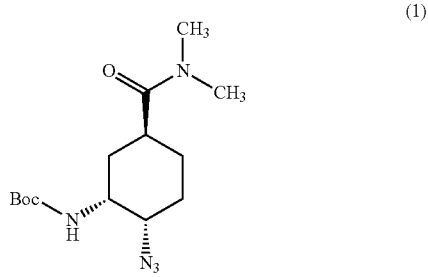 [SMILES: CN(C)C(=O)[C@H]1CC[C@H](N=[N+]=[N-])[C@H](NC(=O)OC(C)(C)C)C1]

wherein Boc represents a tert-butoxycarbonyl group,
the method comprising:
(i) adding a 1-dodecylpyridinium salt and a metal azide salt to water to prepare an aqueous solution of an azidification reagent complex comprising 1-dodecylpyridinium salt-metal azide salt, and
subsequently performing azeotropic dehydration of the azidification reagent complex by adding the azidification reagent complex to an aromatic hydrocarbon solvent to form a mixed solution comprising the azidification reagent complex and the aromatic hydrocarbon solvent, wherein the water content of the mixed solution is 0.2% or less; and (ii) adding, to the mixed solution prepared in step (i), a compound (2) represented by the following formula:

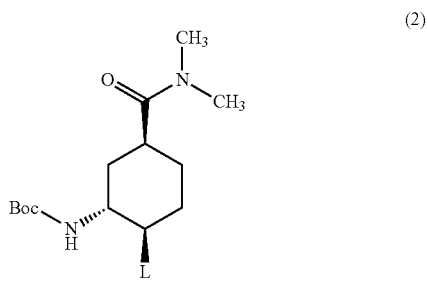

wherein Boc is as defined above; and L represents a leaving group, wherein the leaving group represents a (C1 to C2 alkyl)sulfonyloxy group (wherein the C1 to C2 alkyl group may have one or more identical or different halogeno groups as substituents) or a benzenesulfonyloxy group (wherein the benzene ring may have one or more identical or different groups as substituents selected from a halogeno group, a methyl group, and a nitro group).

2. The production method according to claim 1, wherein L is a methanesulfonyloxy group or an ethanesulfonyloxy group.

3. The production method according to claim 1, wherein L is a methanesulfonyloxy group.

4. The production method according to claim 1, wherein the 1-dodecylpyridinium salt is 1-dodecylpyridinium chloride.

5. The production method according to claim 1, wherein the amount of the 1-dodecylpyridinium salt used is stoichiometrically in the range of 0.45 to 0.55 molar equivalent with respect to compound (2).

6. The production method according to claim 1, wherein the metal azide salt is sodium azide or lithium azide.

7. The production method according to claim 1, wherein the amount of the metal azide salt used is stoichiometrically in the range of 1.8 to 2.2 molar equivalents with respect to compound (2).

8. The production method according to claim 1, wherein the aromatic hydrocarbon solvent is one selected from benzene, toluene, xylene, chlorobenzene, and dichlorobenzene or a mixed solvent of two or more thereof.

9. The production method according to claim 1, wherein the aromatic hydrocarbon solvent is toluene.

10. The production method according to claim 1, wherein the preparation of the aqueous solution of the azidification reagent complex is performed by adding a 1-dodecylpyridinium salt and a metal azide salt to water and then stirring the mixture at an internal temperature of 20 to 40° C.

11. The production method according to claim 10, wherein the stirring is performed for 0.5 hour or longer.

12. The production method according to claim 1, wherein the azeotropic dehydration is performed by adding the aqueous solution of the azidification reagent complex dropwise to the aromatic hydrocarbon solvent under heating.

13. The production method according to claim 1, wherein the aqueous solution of the azidification complex reagent in step (i) is prepared by adding the 1-dodecylpyridinium salt and the metal azide salt to the water and stirring the aqueous solution of the azidification complex to an internal temperature of 20 to 40° C. for 0.5 hour or longer, and wherein the azeotropic dehydration is performed by adding the azidification reagent complex dropwise to the aromatic hydrocarbon solvent under heating to form the mixed solution.

14. A method for producing a compound (4) represented by the following formula:

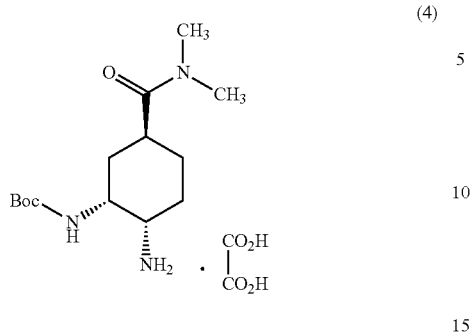
(4)

the method comprising the steps of claim 1 followed by steps of:
(i) reducing compound (1) produced by the production method according to claim 1:

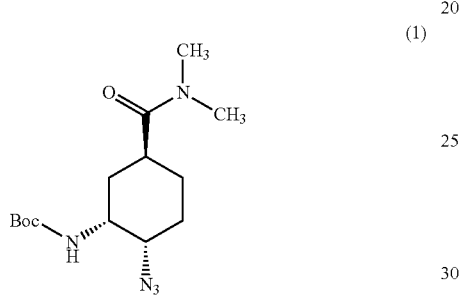
(1)

wherein Boc is as defined above, to obtain a compound (3) represented by the following formula or a salt thereof, or a solvate thereof:

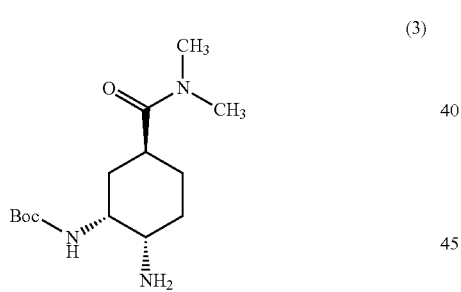
(3)

wherein Boc is as defined above; and
(ii) treating compound (3) with oxalic acid to obtain compound (4).

15. A method for producing a compound (A-a) represented by the following formula:

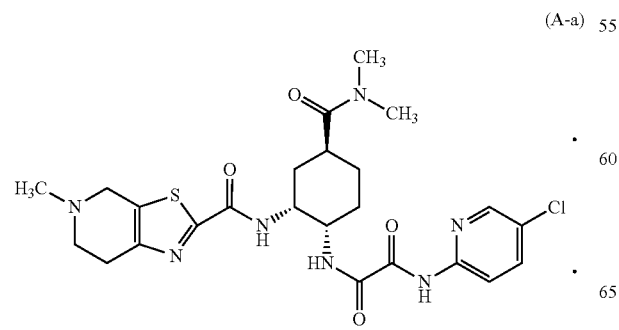
(A-a)

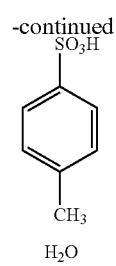

comprising the production method according to claim 1 followed by the steps of:
(i) reducing compound (1) represented by the following formula:

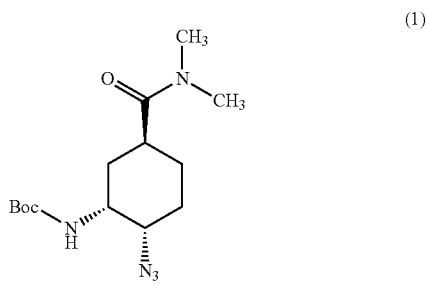 [SMILES: CN(C)C(=O)[C@H]1CC[C@H](N=[N+]=[N-])[C@H](NC(=O)OC(C)(C)C)C1]
(1)

wherein Boc represents a tert-butoxycarbonyl group, to obtain a compound (3) represented by the following formula or a salt thereof, or a solvate thereof:

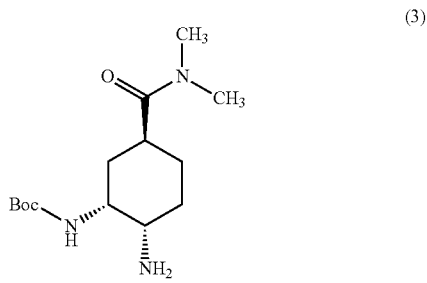
(3)

wherein Boc is as defined above;
(ii) treating compound (3) or the salt thereof, or the solvate thereof with oxalic acid to obtain a compound (4) represented by the following formula:

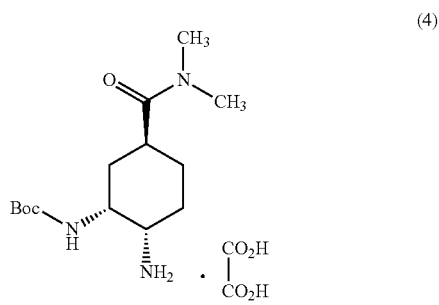
(4)

wherein Boc is as defined above;

(iii) treating the compound (4) with a compound (7) represented by the following formula:

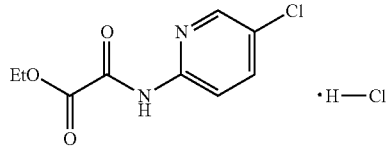
(7)

in the presence of a base to obtain a compound (8) represented by the following formula:

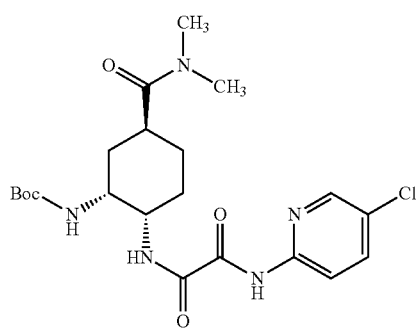
(8)

wherein Boc is as defined above;

(iv) deprotecting a Boc group in compound (8) to obtain a compound (9) represented by the following formula or a salt thereof:

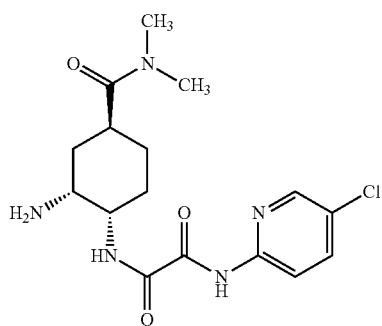
(9)

condensing compound (9) or the salt thereof with a compound (10) represented by the following formula:

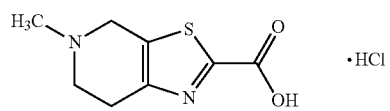
(10)

to obtain a compound (A) represented by the following formula:

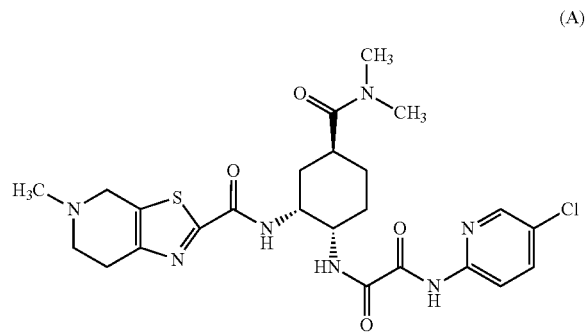 [SMILES: CN1CCc2nc(C(=O)N[C@@H]3C[C@@H](C(=O)N(C)C)CC[C@@H]3NC(=O)C(=O)Nc3ccc(Cl)cn3)sc2C1]
(A)

and (v) treating compound (A) with p-toluenesulfonic acid or a hydrate thereof to obtain compound (A-a).

16. A method for producing a compound (1) represented by the following formula:

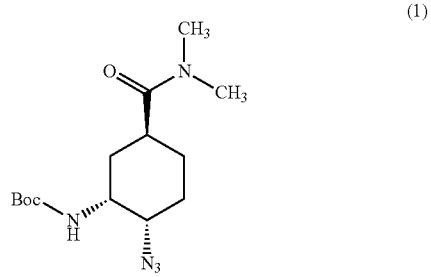 [SMILES: CN(C)C(=O)[C@H]1CC[C@H](N=[N+]=[N-])[C@H](NC(=O)OC(C)(C)C)C1]
(1)

wherein Boc represents a tert-butoxycarbonyl group, the method comprising:

(i) adding an amount of 1 dodecylpyridinium salt and an amount of a metal azide salt to water to prepare an aqueous solution of an azidification reagent complex comprising 1 dodecylpyridinium salt-metal azide salt, and subsequently performing azeotropic dehydration of the azidification reagent complex by adding the azidification reagent complex to an aromatic hydrocarbon solvent to form a mixed solution comprising the azidification reagent complex and the aromatic hydrocarbon solvent, wherein the water content of the mixed solution is 0.2% or less; and (ii) adding, to the mixed solution prepared in Step (i), a compound (2) represented by the following formula:

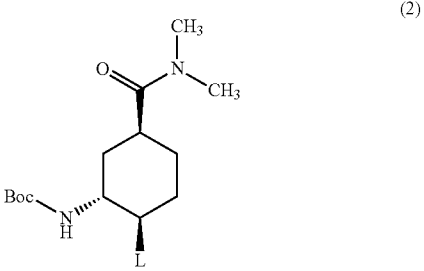
(2)

wherein Boc is as defined above; and L represents a leaving group, wherein the leaving group represents a (C1 to C2 alkyl)sulfonyloxy group (wherein the C1 to C2 alkyl group may have one or more identical or different halogeno groups as substituents) or a benzenesulfonyloxy group (wherein the benzene ring may have one or more identical or different groups as substituents selected from a halogeno group, a methyl group, and a nitro group),
wherein the amount of the 1 dodecylpyridinium salt added in Step (i) is stoichiometrically in the range of 0.45 to 0.55 molar equivalent with respect to compound (2) in Step (ii), and
wherein the amount of the metal azide salt added in Step (i) is stoichiometrically in the range of 1.8 to 2.2 molar equivalents with respect to compound (2) in Step (ii).

17. The production method according to claim 1, wherein the compound (1) produced by the method is obtained at a yield of 71 to 75%.

18. The production method according to claim 16, wherein the compound (1) produced by the method is obtained at a yield of 71 to 75%.

\* \* \* \* \*